United States Patent [19]

Skurkovich et al.

[11] Patent Number: 5,626,843
[45] Date of Patent: May 6, 1997

[54] TREATMENT OF AUTOIMMUNE DISEASES, INCLUDING AIDS, BY REMOVEL OF INTERFERONS, TNFS AND RECEPTORS THEREFOR

[75] Inventors: Simon V. Skurkovich, Rockville, Md.; Boris Skurkovich, Pawtucket, R.I.

[73] Assignee: Advanced Biotherapy Concepts, Inc., Rockville, Md.

[21] Appl. No.: 25,408

[22] Filed: Feb. 26, 1993

[51] Int. Cl.$^6$ ............................................. A61K 39/395
[52] U.S. Cl. ............................................. 424/140.1; 604/6
[58] Field of Search ...................... 424/140.1; 436/547; 604/5, 6

[56] References Cited

U.S. PATENT DOCUMENTS

| | | |
|---|---|---|
| 4,362,155 | 12/1982 | Skurkovich . |
| 4,605,394 | 8/1986 | Skurkovich et al. . |
| 4,824,432 | 4/1989 | Skurkovich et al. . |
| 5,231,024 | 7/1993 | Moller et al. . |

OTHER PUBLICATIONS

Fahey et al. Clin Exp Immunol., 88: 1–5, 1992.
Skurkovich et al., Medical Hypotheses 41: 177–185, 1993.
Harris et al. Tibtech 11: 42–44, 1993.
Co et al., Nature 351: 501–2, 1991.

*Primary Examiner*—Toni R. Scheiner
*Attorney, Agent, or Firm*—Evelyn H. McConathy

[57] ABSTRACT

The present disclosure concerns a treatment for autoimmune diseases, including AIDS, by removing interferons, TNFs and receptors therefor, from body fluids. An extracorporeal device exposes fluids from a patient, including blood, plasma, cerelorospinal fluid, and the like, to an immunosorbent to accomplish removal. Following treatment, the fluid is returned to its source.

16 Claims, 1 Drawing Sheet

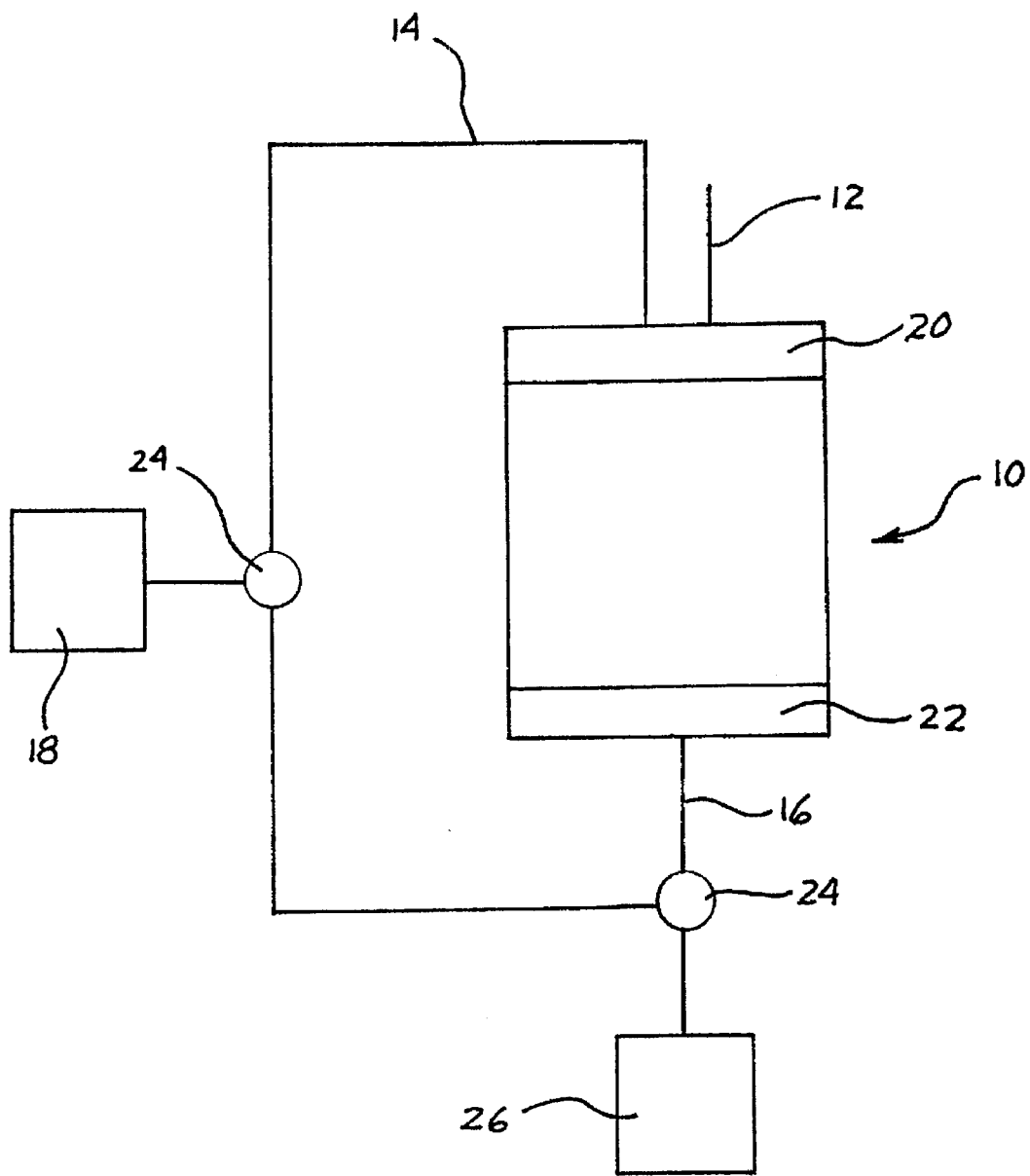

TREATMENT OF AUTOIMMUNE DISEASES, INCLUDING AIDS, BY REMOVEL OF INTERFERONS, TNFS AND RECEPTORS THEREFOR

BACKGROUND OF THE INVENTION a) Field of the Invention

The invention concerns a method to treat conditions and diseases which are caused by the disturbance of synthesis of interferons (IFNs) and certain other substances (e.g., tumor necrosis factor) which damage the immune system and have a direct pathological action on cells.

b) Description of Related Art

Besides its anti-virus and anti-proliferative roles, IFN also plays a role as an immunoregulator (Immunology 25: 367, 1973; W. Stewart, Interferon System, 1979). The normal functioning of the interferon system in vivo is critical for the normal functioning of the immune system. A change in IFN synthesis can bring about a change in the immune system. In 1974 an article was published suggesting that the hyperproduction of IFN can be the main cause of the development of autoimmune disease (Nature 551: 2047, Feb. 22, 1974). IFN was found in the circulation of patients with autoimmune diseases and it was neutralized in vivo with antibody to leukocyte (alpha) IFN; healthy people do not have interferon in their blood (Annals of Allergy 35: 356, 1975).

Later it was shown that this hyperproduced alpha IFN is found not only in the circulation of patients with classic autoimmune diseases, but also in patients with HIV infection (J Infec Dis 146: 451, 1982). This alpha IFN is pH labile while normal alpha IFN is pH stable. This aberrant type of IFN may participate in the pathogenesis of AIDS where its presence is a predictive marker of AIDS progression (Cancer Res 46: 417, 1986). It was proposed to remove aberrant IFN from the circulation as a method of treatment of patients with autoimmune disease and AIDS, also considered an autoimmune disease.

Aberrant IFN can induce tumor necrosis factor (TNF) and its receptors (AIDS Research and Human Retroviruses 7: 545, 1991), which enhances virus replication (Proc Natl Acad Sci USA 86: 2365, 1989). In other words, aberrant IFN production reflects virus replication. The aberrant IFN induced by HIV has low anti-(HIV) viral activity (J Immunol 148: 422, 1992). In some stages of AIDS, its induction may help the virus survive.

Alpha IFN, mostly the aberrant type, may be the main cause of the development of autoimmune disease, but in some situations gamma IFN, and more rarely beta IFN, can also play a pathogenetic role since all of these participate in immune regulation. Every hyperproduction and chronic circulation of IFNs, especially aberrant IFNs, and other defective IFNs, have a negative influence on the function of different body systems, in particular the immune system (J of Clin Immunol and Immunopathol 43: 362, 1987; Am J of Med Sci 295: 532, 1988). The presence in AIDS patients of gamma IFN may be a marker of the intensification of the autoimmune process.

Besides being present in the circulation, IFNs have also been found in the cerebrospinal fluid in some patients with psychiatric and neurologic diseases (Acta Biol Med Germ 38: 879, 1979; Acta Neurol Scand 53: 152, 1976) and in the joint synovial fluid (Ann of Rheum Dis 42: 672, 1983) of patients with rheumatoid arthritis. Healthy people do not have interferons in the spinal or synovial fluids.

As is known, AIDS is induced by HIV. In autoimmune disease, where HIV like particles and their antibodies against them were found in the sera of humans and in animal models, it is possible that the particles are integral parts of the lymphocytes or organs. HIV and its particles are interferon inducers. Every antigen is an interferonogen; "self" cannot induce IFN. Thus, the production of IFN signals the invasion by a foreign antigen. IFN production, mostly IFN of the aberrant type, and its prolonged circulation in the body is an inseparable part of the development of autoimmune disease and triggers immunological chaos. For example, antibodies to CD4 in patients with HIV infection (Am J of Med 78: 621, 1985), can crossreact with class II antigen (Proc Natl Acad Sci USA 88: 3060, 1991) which in turn is induced by gamma IFN, or by gamma IFN in combination with TNF, and possibly by aberrant IFN, which induces TNF. In other words, aberrant IFN and TNF could be important pathological triggers of immune dysregulation in AIDS.

Besides classic AD and AIDS, there are a number of other pathological conditions in which autoantibodies play a pathogenic role. After cell (or organ) transplantation and after heart attack or stroke, certain antigens from the transplantation of cells (organs) or necrotic cells from the heart or the brain can stimulate the production of antibodies or immune lymphocytes (R. Johnson, L. Lynne and Wm. Seldin, Sem Nuc Med 19: 238, 1989; M. Leinonen, E. Linnanmaki, K. Mattile and M. S. Nieminen, et al., Microbiolo Path 9: 67, 1990; J. Montalban, A. Codin, J. Ordi, M. Vilardell, et al., Stroke 22: 750, 1991), which later participate in rejection (in the case of a transplant) or attack the cardiac and brain cells, aggravating the condition. Every antigen stimulation is accompanied by the immediate synthesis of interferon which triggers the immune process. To counter transplant rejection, antibodies to three kinds of interferons (alpha, beta, and gamma), or in some cases, gamma IFN alone, and the antigen of the transplanted cell or organ are placed in the immunosorbent column. To treat infarction or stroke, antibodies to IFNs as well as cardiac or brain antigens are placed in the immunosorbent column. Further, the present invention may be used in combination with immunosuppressive therapy necessary for treating infarction and stroke.

In addition, in human autoimmune disease certain cells express abnormally elevated levels of HLA class II antigens, which is stimulated by the disturbed production of gamma IFN and TNF (IFN 9, Academic Press 1987, p. 75). The disturbance of the synthesis of HLA class II antigen plays an important role in the pathogenesis of autoimmune disease and AIDS. The disturbance of HLA class II antigen leads to a disturbance of the presentation of antigens to T cells, T/B cooperation and the dysregulation of the interaction between T cells. For the normalization of the immune system, it is necessary to remove hyperproduced class II antigens, and in some cases, it is also necessary to remove its receptors. For this reason, the present invention includes in the immunosorbent antibody to class II antigens, and in some cases, antibody to its receptors. This absorption can be obtained from whole blood or from the plasma with leukocytes

SUMMARY OF THE INVENTION

An objective of the present invention is to restore immunity in some autoimmune diseases, such as AIDS, by removing IFNs together with TNF, and in some cases the receptors therefor, as well as certain antibodies and antigens, using combinations of immunosorbents in an extracorporeal device. An example of antibody use is placing antibody to HLA class II antigen in the immunosorbent. An example of using antigen in an immunosorbent is the antigen—CD4.

The latter can be included among the immunosorbents, either in combination with other sorbents, or alone. For example, in treating AIDS patients, a combined sorbent comprising a first component of antibodies to IFNs, a second component of lymphocytes from healthy donors, mostly CD4 cells to absorb serum antibodies which react with CD4 cells, and a third component to remove TNF can be used. In rheumatoid arthritis, antigens from joints, skin and possibly other target antigens can be used as sorbents in addition to antibodies to IFNs and other sorbents. In autoimmune diseases of the central nervous system, additional immunosorbents antigens from the brain cells could be used to absorb antibodies formed against brain cells. In treating patients with systemic lupus erythematosus, in addition to other sorbents, a sorbent (DNA) can be added to absorb anti-DNA antibodies.

In still another example of treating an autoimmune disease, e.g., rheumatoid fever, the invention uses one sorbent for removing IFNs and other substances, often together with their receptors, and a second sorbent for removing antibodies against cardiac tissue. The second sorbent can also include both certain serotypes of streptococcus (streptococcus group "A") and antigens of cardiac tissue. Some antigens from cardiac tissue and some serotypes of streptococcus are antigenically similar. When treating certain diseases connected with hypersensitivity of the immediate type, e.g., bronchial asthma, a combined sorbent having a first component for absorbing IFNs and other substances, as well as a second component made of an antibody against IgE (immunoglobulin E), can be used.

These approaches could restore the immune system and, especially in AIDS, break the chain of events which are insuring the continuous replication and survival of the virus, HIV.

Removal or neutralization of alpha, gamma and beta IFNs, TNF, and HLA II class antigen, and/or their receptors in some cases, as well as other components, can be accomplished with polyclonal or monoclonal antibodies produced in mice or human hybridoma. These different antibodies can also be put in an immunosorbent column. If the antibody is to be administered intramuscularly or intravenously, then it is preferable to use monoclonal antibody produced in human hybridoma (any monoclonal antibody, however it is produced, as long as it comprises human protein). To neutralize antibodies to different cell antigens, the antigens from these cells must be placed directly in the immunosorbent column. It is also possible to use a combined treatment—with both the immunosorbent column and parenteral injection of specific antibody.

Regarding the extracorporeal system, these substances can be obtained with an extracorporeal device from whole blood, plasma with leukocytes, or plasma only. To do this, one can use a blood cell separator (e.g., Cobe "Spectra") to which the immunosorbent column is connected. Such a device is known from U.S. Pat. No. 4,362,155 which is incorporated herein by reference. To remove pathological substances from joint and spinal fluids, a special extracorporeal device with a small amount of immunosorbent is used.

BRIEF DESCRIPTION OF THE DRAWING

The sole figure shows an extracorporeal device for removing pathological substances from joint and spinal fluids.

DESCRIPTION OF THE PREFERRED EMBODIMENT

The column 10 and tubing are made of plastic approved for the use of blood. The total volume of the column 10 and tubing is small, approximately 30–35 ml. The column 10 is filled with the immunosorbent, consisting of the antigen or antibody bound to Sepharose 4B or another suitable matrix, through a short filling tube 12 placed at a first end of the column 10. Input tube 14 and return tube 16 are connected between the first end and a second end, respectively, of the column 10, and a fluid sample 18. A first filter 20 is interposed between the input tube 14 and the column 10, and a second filter 22 is interposed between the return tube 16 and the column 10. The filters 20, 22 prevent the flow of immunosorbent from the column 10. Two way stopcocks 24, 24 regulate flow throughout the system.

The column 10 is positioned lower than the source of the fluid sample 18, whereupon the cerebrospinal or synovial fluid flows into the column 10 under the influence of gravity. After the fluid perfuses through the immunosorbent, it is collected in a holding tube 26 from which it is returned to the source of the fluid.

Materials according to the present invention to be used with the column 10 may be obtained as follows:

EXAMPLE 1

Production of antibody to human gamma IFN: Adult rabbits are immunized with purified human gamma IFN ($10^5$–$10^6$ unit/mg protein). This interferon is first mixed with equal volumes of Freund's Complete Adjuvant and 30% Arlacel A and injected IM or subcutaneously on day 1, 4, 14 and 43 (100 units, 200 units, 200, 200 respectively). After this 200,000 units/month for 6 additional months are injected. The serum is obtained when the titer has reached 100 units (1 unit of antibody neutralizes 10 units of gamma IFN). IgG is isolated and purified.

EXAMPLE 2

Production of antibody to human beta IFN: Adult sheep receive 12 weekly injections of $10^7$ of human beta IFN. Six weeks after the 12 injections a booster shot of $2.7 \times 10^7$ units of IFN is given which is first mixed with Freund's Complete Adjuvant and injected into several IM sites. Bleeding begins 7 days later. IgG is then obtained and purified.

EXAMPLE 3

Column Preparation: Sepharose CL-4B (Pharmacia, Piscattawy, N.J.) (100 ml) is washed thoroughly with pyrogen free water, then suspended in 300 ml ice cold 1M $NaCO_3$ pH 11.0. 20 gms CNBr in 10 ml acetonitrile is added to the Sepharose. After 2 minutes this is collected on a fretted glass funnel. Sepharose cake is washed with 5 volumes of ice cold 0.2M Na Bicarbonate buffer pH 9.5 and 5 volumes of ice cold 0.5M Na Bicarbonate buffer pH 8.5. This is immediately resuspended in a solution of 780 mg anti-alpha IFN antibody in 200 ml of 0.2M Bicarbonate buffer pH 9.3. This is incubated for 20 hours at 4 degrees C. This is then centrifuged, the supernatant is decanted and sediment is resuspended in 100 ml of 0.05 PBS (Phosphate buffered saline) and 2M glycine pH 8.0 for 12 hours at room temperature. This is then washed thoroughly with 20 volumes of PBS.

What is claimed is:

1. A method of removing antigens from a patient with autoimmune disease or AIDS comprising the steps of:

drawing fluid from said patient;

passing said fluid through immunosorbent comprising a combination of antibodies, consisting essentially of: (a) one or more antibodies to at least one interferon, selected from the group consisting of alpha interferons and gamma interferons, and receptors therefor; and (b) one or more antibodies to tumor necrosis factors, and receptors therefor; and returning said fluid to said patient.

2. The method according to claim 1, wherein said method removes alpha interferon and tumor necrosis factor from said fluid.

3. The method according to claim 1, wherein said method removes gamma interferon and tumor necrosis factor from said fluid.

4. The method according to claim 1, wherein said method removes both alpha and gamma interferon, and tumor necrosis factor, from said fluid.

5. The method according to claim 1, wherein said fluid is selected from the group consisting essentially of blood, plasma, plasma containing leukocytes, peritoneal fluid, cerebrospinal fluid, and synovial fluid.

6. The method according to claim 1, wherein said antibodies are selected from the group consisting of monoclonal antibodies, polyclonal antibodies, and combinations thereof.

7. The method according to claim 1, wherein said method removes: (a) one or more receptors for at least one interferon, selected from the group consisting of alpha interferons and gamma interferons, and (b) tumor necrosis factor, from said fluid.

8. The method according to claim 1, wherein said method removes: (a) one or more interferons, selected from the group consisting of alpha interferons and gamma interferons, and (b) at least one receptor for tumor necrosis factor, from said fluid.

9. The method according to claim 1, wherein said method removes (a) one or more receptors for at least one interferon, selected from the group consisting of alpha interferons and gamma interferons, and (b) at least one receptor for tumor necrosis factor, from said fluid.

10. A method of removing antigens from a patient with autoimmune disease or AIDS comprising the steps of:

drawing fluid from a patient;

passing said fluid through immunosorbent comprising in combination a plurality of antibodies, consisting essentially of at least one antibody selected from the group consisting of anti-alpha interferon and antibody to alpha interferon receptor, and at least one antibody selected from the group consisting of anti-gamma interferon and antibody to gamma interferon receptor; and returning said fluid to said patient.

11. The method according to claim 10, wherein said fluid is selected from the group consisting essentially of blood, plasma, plasma containing leukocytes, peritoneal fluid, cerebrospinal fluid, and synovial fluid.

12. The method according to claim 10, wherein said antibodies are selected from the group consisting of monoclonal antibodies, polyclonal antibodies, and combinations thereof.

13. The method according to claim 10, wherein said treatment removes both alpha interferon and gamma interferon from said fluid.

14. The method according to claim 10, wherein said treatment removes both alpha interferon receptor and gamma interferon receptor from said fluid.

15. The method according to claim 10, wherein said treatment removes a combination of: (a) alpha interferon, and (b) receptor for gamma interferon, from said fluid.

16. The method according to claim 10, wherein said treatment removes a combination of: (a) at least one receptor for alpha interferon, and (b) gamma interferon, from said fluid.

* * * * *